United States Patent [19]

Pelosi, Jr.

[11] 3,971,811

[45] July 27, 1976

[54] 5-(4-CHLOROPHENYL)-2-FURYL PHENYL KETONE

[75] Inventor: Stanford S. Pelosi, Jr., Norwich, N.Y.

[73] Assignee: Morton-Norwich Products, Inc., Norwich, N.Y.

[22] Filed: June 16, 1975

[21] Appl. No.: 586,874

[52] U.S. Cl. .............................. 260/347.8; 424/285
[51] Int. Cl.$^2$ ........................................ C07D 307/46
[58] Field of Search ................................. 260/347.8

[56] References Cited
UNITED STATES PATENTS 3,801,605   4/1974   Carson ............................ 260/347.5

OTHER PUBLICATIONS

Bou–Hoi, et al., Chem. Abst., vol. 45, col. 7104–7105 (1951).

Tsuchiya, Chem. Abst., vol. 59, col. 2751 (1963).

*Primary Examiner*—Harry I. Moatz
*Attorney, Agent, or Firm*—Anthony J. Franze

[57] ABSTRACT

5-(4-chlorophenyl)-2-furyl phenyl ketone is an effective anthelmintic agent.

1 Claim, No Drawings

5-(4-CHLOROPHENYL)-2-FURYL PHENYL KETONE

This invention relates to the compound 5-(4-chlorophenyl)-2-furyl phenyl ketone of the formula:

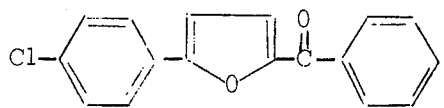

This compound is distinguished by its ability to combat helminth infection. When administered by gavage as a suspension in aqueous solution to mice harboring *Ascaris suum* worms, this compound, in a dose of 100 mg/kg, accomplished a 57 percent reduction of the worm burden.

The compound of this invention is readily prepared by reaction of benzoyl chloride with 2-(4-chlorophenyl)furan in the presence of aluminum chloride. The method now preferred is briefly described:

To a solution of 80 g (0.60 mole) of $AlCl_3$ in 435 ml of $CS_2$ was added 84 g (0.60 mole) of benzoyl chloride. A solution of 107 g (0.60 mole) of 2-(4-chlorophenyl)-furan in 280 ml of $CS_2$ was added dropwise while maintaining the temperature between 10°–15° by means of an ice bath. The reaction mixture was stirred at 15°–20° for 30 minutes, at room temperature for 30 minutes, and added to 2000 ml of ice/water. The aqueous layer was separated from the $CS_2$ layer and extracted with 2 × 500 ml portions of dichloromethane. The $CS_2$ and $CH_2Cl_2$ layers were combined, washed with 1 × 1000 ml of 6% sodium carbonate solution and with 1000 ml of water, and dried over magnesium sulfate. The solvent was removed on a rotary evaporator to yield a brown solid which was recrystallized from acetonitrile (Darco) twice to yield 16 g (11%) of product. An analytical sample was prepared by during a sample at room temperature in the vacuum pistol, m.p. 128°–130°.

Anal. Calcd. for $C_7H_{11}ClO_2$: C, 72.22; H, 3.92. From: C, 71.93; H, 3.89.

What is claimed is:

1. The compound 5-(4-chlorophenyl)-2-furyl phenyl ketone of the formula:

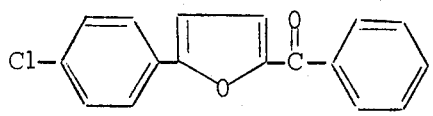

* * * * *